US008641987B2

(12) United States Patent
Sandell (10) Patent No.: US 8,641,987 B2
(45) Date of Patent: Feb. 4, 2014

(54) SAMPLE CHAMBER ARRAY AND METHOD FOR PROCESSING A BIOLOGICAL SAMPLE

(75) Inventor: Donald R. Sandell, San Jose, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 1825 days.

(21) Appl. No.: 10/351,633

(22) Filed: Jan. 24, 2003

(65) Prior Publication Data

US 2004/0146869 A1 Jul. 29, 2004

(51) Int. Cl.
*B01L 3/00* (2006.01)
(52) U.S. Cl.
USPC .............................. 422/503; 422/501; 422/502
(58) Field of Classification Search
USPC .................... 422/100, 102, 503, 501, 502
See application file for complete search history.

(56) References Cited

U.S. PATENT DOCUMENTS

| | | | |
|---|---|---|---|
| 4,522,622 A * | 6/1985 | Peery et al. | 604/191 |
| 4,805,767 A * | 2/1989 | Newman | 206/219 |
| 4,858,883 A * | 8/1989 | Webster | 251/61.1 |
| 5,038,852 A | 8/1991 | Johnson et al. | |
| 5,333,675 A | 8/1994 | Mullis et al. | |
| 5,475,610 A | 12/1995 | Atwood et al. | |
| 5,656,493 A | 8/1997 | Mullis et al. | |
| 5,863,502 A * | 1/1999 | Southgate et al. | 422/58 |
| 5,928,907 A | 7/1999 | Woudenberg et al. | |
| 6,015,674 A | 1/2000 | Woudenberg et al. | |
| 6,193,088 B1 | 2/2001 | Vincent et al. | |
| 6,272,939 B1 | 8/2001 | Frye et al. | |
| 6,280,148 B1 | 8/2001 | Zengerle et al. | |
| 2002/0092767 A1 | 7/2002 | Bjornson et al. | |
| 2002/0185184 A1 | 12/2002 | O'Connor et al. | |

FOREIGN PATENT DOCUMENTS

| | | |
|---|---|---|
| EP | 0 606 534 B1 | 12/1997 |
| WO | WO 01/15807 A1 | 3/2001 |
| WO | WO 02/00347 A2 | 1/2002 |

* cited by examiner

*Primary Examiner* — Natalia Levkovich (57) ABSTRACT

A sample chamber array is provided. The sample chamber array may comprise at least one reservoir in fluid communication with at least one sample chamber, and a movable portion defining the sample chamber. The reservoir is fillable with a liquid biological sample. The movable portion may be movable with respect to the remainder of the sample chamber from a first position to a second position. In the first position the movable portion is concave and the sample chamber is without biological sample. In the second position the movable portion is convex and the sample chamber comprises biological sample. The movement of the movable portion to the second position causes a pressure drop to transport the biological sample into the sample chamber from the at least one reservoir. Methods for processing a biological sample and methods of making a sample chamber array are also provided.

10 Claims, 12 Drawing Sheets

SAMPLE CHAMBER ARRAY AND METHOD FOR PROCESSING A BIOLOGICAL SAMPLE

FIELD

The present teachings relate generally to a sample chamber array configured for samples of biological material, and methods of processing a biological sample using a sample chamber array. The present teachings further relate, in various aspects, to a sample chamber array that has a movable portion of a sample chamber that causes the sample chamber to be filled with a biological sample.

BACKGROUND

Biological testing has become an important tool in detecting and monitoring diseases. In the biological testing field, thermal cycling is used to amplify nucleic acids by, for example, performing polymerase chain reactions (PCR) and other reactions. PCR, for example, has become a valuable research tool with applications such as cloning, analysis of genetic expression, DNA sequencing, and drug discovery. Methods such as PCR may be used to detect a reaction of a test sample to an analyte-specific reagent. Typically, an analyte-specific reagent is placed in each sample chamber in advance of performing the biological testing. The test sample is then later inserted into the sample chambers, and the sample tray or microcard is then thermally cycled.

Recent developments in the field have led to an increased demand for biological testing devices. Biological testing devices are now being used in an increasing number of ways. It is desirable to provide a more efficient and compact method and structure for filling and thermally cycling substrates such as sample trays and microcards.

In typical systems, the sample tray or microcard is loaded with reagent, then loaded with the test sample, and then transported and inserted into a separate device for thermal cycling. It is desirable to reduce the amount of time and number of steps taken to fill and thermally cycle a sample tray or microcard.

SUMMARY

In accordance with various aspects of the present teachings, a sample chamber array is provided. The sample chamber array may comprise at least one reservoir in fluid communication with at least one sample chamber, and a movable portion defining the sample chamber. The reservoir is fillable with a liquid biological sample. The movable portion may be movable with respect to the remainder of the sample chamber from a first position to a second position. In the first position the movable portion is concave and the sample chamber is without biological sample. In the second position the movable portion is convex and the sample chamber comprises biological sample. The movement of the movable portion to the second position causes a pressure drop to transport the biological sample into the sample chamber from the at least one reservoir.

In a further aspect, a method for processing a biological sample is provided. The method comprises providing a sample chamber array comprising at least one reservoir in fluid communication with at least one sample chamber, filling the reservoir with the biological sample, and moving the sample chamber from a concave position to a convex position. The moving of the sample chamber generates a pressure drop to transport the biological sample from the reservoir to the sample chamber.

In a yet further aspect of the present teachings, a method of making a sample chamber array is provided. The method comprises providing a first member comprising at least one chamber base, providing a second member comprising at least one movable portion, positioning the first member and the second member to align the chamber base and the movable portion, and affixing the first member to the second member. The affixing the first member to the second member forms at least one reservoir between the first member and the second member. In various aspects, the chamber base and the movable portion are concave.

It is to be understood that both the foregoing general description and the following description of various embodiments are exemplary and explanatory only and are not restrictive.

BRIEF DESCRIPTION OF THE DRAWINGS

The accompanying drawings, which are incorporated in and constitute a part of this specification, illustrate several exemplary embodiments. In the drawings.

DESCRIPTION OF VARIOUS EMBODIMENTS

Reference will now be made to various exemplary embodiments, examples of which are illustrated in the accompanying drawings. Wherever possible, the same reference numbers are used in the drawings and the description to refer to the same or like parts.

In accordance with various embodiments, a sample chamber array is provided having a plurality of sample chambers. In one aspect, the sample array comprises a plurality of sample chambers, each in fluid communication with a reservoir via a fill channel.

Figure 1:
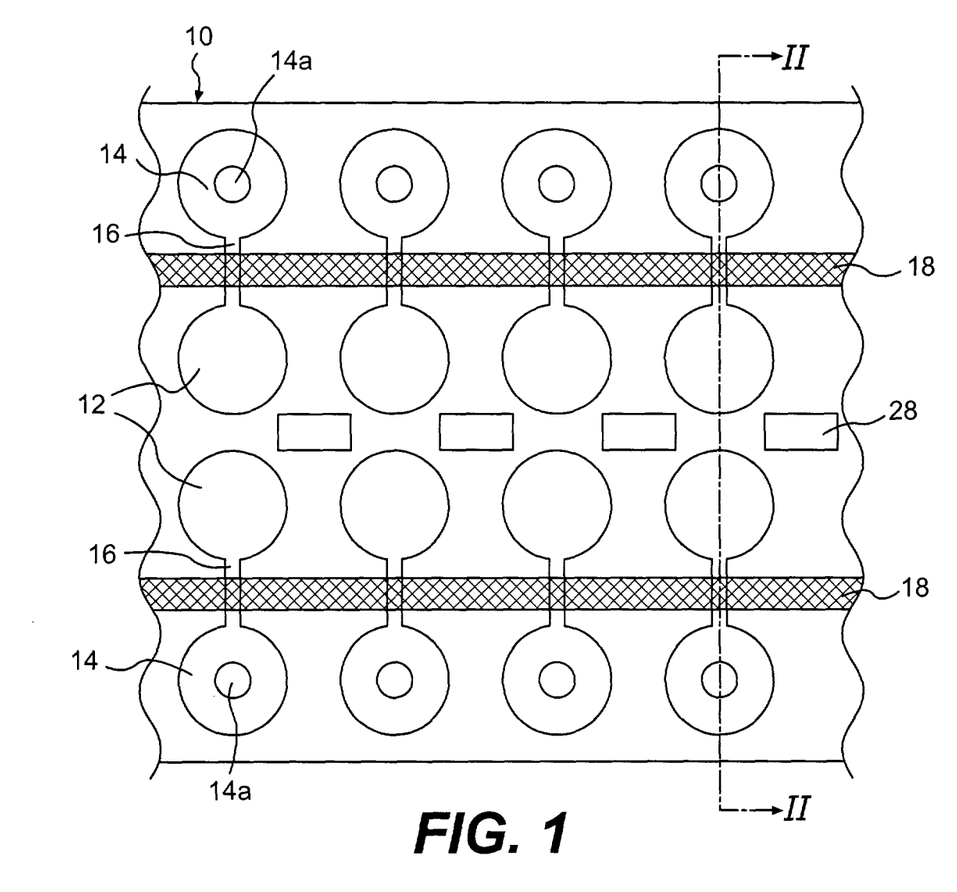
FIG. 1 is partial plan view of a section of a sample chamber array according to an exemplary embodiment.

In various embodiments, such as the embodiment shown in FIG. 1, a sample chamber array 10 with a plurality of sample chambers is disclosed. In various embodiments, the sample chamber array 10 is in the form of a tape. In other various embodiments, the sample chamber array may be a rigid or flexible sample tray or microcard. It should be understood that the sample chamber array may be placed on any other type of suitable medium.

Sample chamber array 10 may be configured for thermally cycling samples of biological material in a thermal cycling device. The thermal cycling device may be configured to perform nucleic acid amplification on samples of biological material. One common method of performing nucleic acid amplification of biological samples is polymerase chain reaction (PCR). Various PCR methods are known in the art, as described in, for example, U.S. Pat. Nos. 5,928,907 and 6,015,674 to Woudenberg et al., the complete disclosures of which are hereby incorporated by reference for any purpose. Other methods of nucleic acid amplification include, for example, ligase chain reaction, oligonucleotide ligations assay, and hybridization assay. These and other methods are described in greater detail in U.S. Pat. Nos. 5,928,907 and 6,015,674.

In various embodiments, the sample chamber array may be used in a thermal cycling device that performs real-time detection of the nucleic acid amplification of the samples in the sample chamber array during thermal cycling. Real-time detection systems are known in the art, as also described in greater detail in, for example, U.S. Pat. Nos. 5,928,907 and 6,015,674 to Woudenberg et al., incorporated herein above. During real-time detection, various characteristics of the samples are detected during the thermal cycling in a manner known in the art. Real-time detection permits more accurate and efficient detection and monitoring of the samples during the nucleic acid amplification process. Alternatively, the sample chamber array may be used in a thermal cycling device that performs endpoint detection of the nucleic acid amplification of the samples. Several types of detection apparatus are shown in WO 02/00347A2 to Bedingham et al., the complete disclosure of which is hereby incorporated by reference for any purpose.

The sample chamber array may be configured to contact a sample block for thermally cycling the biological materials in the sample chambers of the sample chamber tape section. The sample block may be operatively connected to a temperature control unit programmed to raise and lower the temperature of the sample block according to a user-defined profile. For example, in various embodiments, a user may supply data defining time and temperature parameters of the desired PCR protocol to a control computer that causes a central processing unit (CPU) of the temperature control unit to control thermal cycling of the sample block. Several non-limiting examples of suitable temperature control units for raising and lowering the temperature of a sample block for a microcard or other sample-holding member are described in U.S. Pat. No. 5,656,493 to Mullis et al. and U.S. Pat. No. 5,475,610 to Atwood et al., the disclosures of which are both hereby incorporated by reference for any purpose.

In one embodiment, the sample chamber array comprises at least one fill chamber or reservoir on the sample chamber array, a plurality of sample chambers, and a plurality of fill conduits or channels. One embodiment of a sample chamber array according to the present teachings is shown in FIGS. 1-4. As embodied herein and shown in FIGS. 1-4, the sample chamber array may be in the form of a tape, a microcard, or a sample tray generally designated by reference number 10. The basic structure and operation of the sample chamber array 10 is identical for each of the formats: tape, microcard, or sample tray. As shown in FIGS. 1-4, sample chamber array 10 has a plurality of sample chambers 12, each connected to a reservoir 14 via a fill channel 16.

In various embodiments, each of reservoirs 14 include an opening 14a configured to allow a user to introduce a sample to be tested into reservoir 14, for example by pipetting. Reservoir 14 is configured to contain a volume of fluid sufficient to allow for filling of its corresponding sample chamber 12. Sample chamber 12, when in the expanded position, may be of any suitable volume. In one example, the volume is between 0.1 μL and 1,000 μL, in another example, between 1 μL and 100 μL, and in another example, approximately 5 μL. It should be understood that the sample chambers according to the present teachings can be any size suitable for biological testing. In some embodiments, it may not be possible for all of the fluid contained in reservoir 14 to be transferred into chamber 12, therefore reservoir 14 may have a volume greater than the volume of chamber 12 to ensure a suitable fill.

In various embodiments, sample chamber array 10 may include a section of adhesive material 18 that is configured to allow for sealing off of fill channel 16 after sample chamber 12 has been filled. The filling of the sample chambers as well as the sealing of channel 16 will be described further in reference to FIGS. 2a-2e. Sample chamber array 10 may further include a plurality of regions 28, configured to receive an adhesive label, for example, or other identifying marking or indicator to identify the contents of the sample chambers or any other desirable information.

Figure 4:
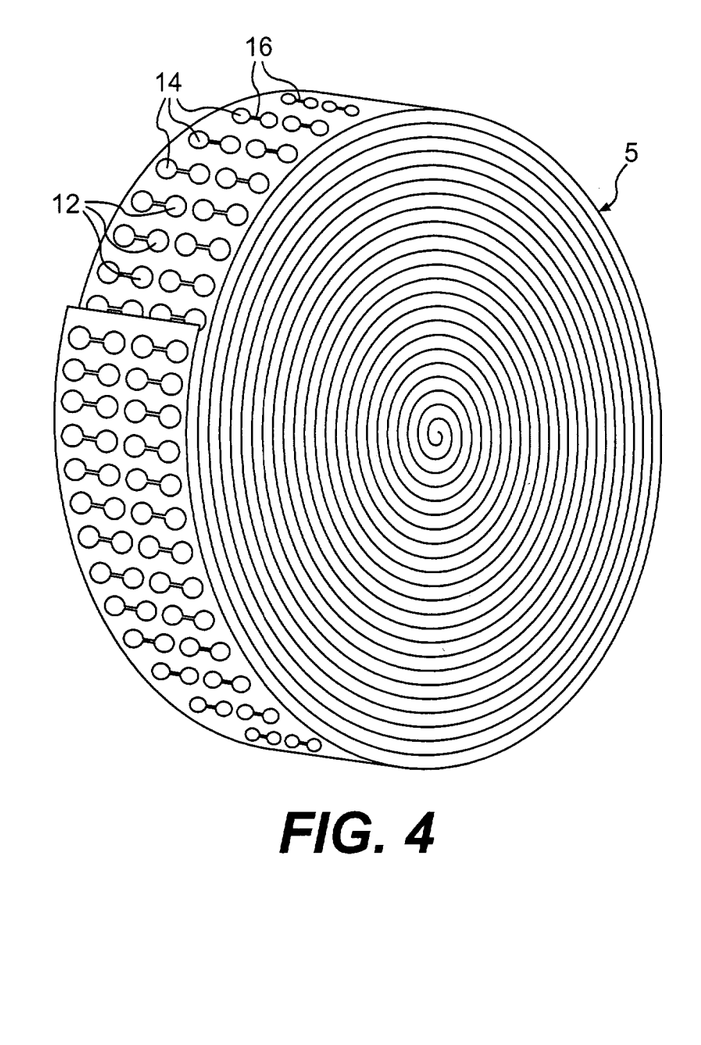
FIG. 4 is a perspective view of a roll of PCR tape having the sample chamber configuration shown in FIG. 1.

FIG. 4 depicts a roll of PCR sample chamber tape 5, from which a sample chamber array, such as sample chamber array 10 could be cut or otherwise obtained. By using a roll 5, a user has the ability to detach the number of sample chambers needed for any particular test without being constrained by a fixed number of sample chambers contained in a sample chamber array. Although sample chamber array 10 is depicted as being a section of roll 5, it could also be manufactured as an array having a set number of sample chambers 12. Sample arrays of the pre-manufactured type may have any number of reservoirs 14 and chambers 12 as desired by a user. It is to be understood that the sample chamber array 10 may be placed on a rigid or flexible microcard or sample tray, instead of the flexible tape 5 shown in FIG. 4.

FIG. 1 depicts a sample chamber array 10 having two rows of chambers, reservoirs, and fill channels. FIGS. 2a-2e depict a cross-section of the sample chamber array 10 generally along line II-II of FIG. 1, which is perpendicular to the length of sample array 10 and passes through an adjacent pair of chambers 12, reservoirs 14, and channels 16. FIGS. 2a-2e depict two rows of chambers, reservoirs, and channels. Alternative embodiments are shown in FIGS. 5-12, but generally operate in a manner similar to the embodiment of FIGS. 1-4, at least regarding the snap-action filling by movement of the movable portion 12b described below. For sake of simplification, the description below will focus on a single row (the top row of FIGS. 2a-2e), although it should be understood that the description applies to the bottom rows of the sample chamber array 10 also.

As shown in FIGS. 2a-2e, a sample chamber array 10 according to the present teachings may comprise a first member 10a affixed to a second member 10b. First and second members 10a, 10b, may be of any material suitable for PCR testing, such as, for example, polypropylene or polyethylene. The first and second members could also be made out of any other suitable material such as aluminum or stainless steel. An embodiment with aluminum or stainless steel could have a thickness in the range of 0.1 mm to 0.2 mm, for example. The first and second members 10a and 10b may be affixed to each other by, for example, a PCR-compatible adhesive, sonic or heat welding, or any other manner known in the art of sample chamber array manufacture.

As depicted in FIGS. 1-4, second member 10b may include a raised portion 14b that, along with first member 10a, defines reservoir 14. Reservoir 14 is typically suitably shaped and sized to contain a predetermined volume of biological sample to be tested. Raised portion 14b is shown in FIGS. 1-4 as being generally cylindrical to define a cylindrical reservoir 14, however it should be understood that raised portion 14b and reservoir 14 can be any other suitable shape such as, for example, square or rectangular. In the embodiment shown, the first member 10a is flat in the region opposite the raised portion 14b of the second member to define the base of reservoir 14. It should be understood that in various embodiments the first member 10a could also include a raised portion, or that in other embodiments, both the first member and the second member could include raised portions so as to define the reservoir for the biological sample to be tested. In order to gain access to reservoir 14 and provide a passage for entry of biological sample into the reservoir, an opening or fill port 14a may be included in the raised portion 14b of second member 10b, as shown in FIGS. 1-2. Alternatively, the opening or fill port could be provided in the base of the reservoir (in first member 10a).

First and second members also define a passage or fill channel 16 between reservoir 14 and sample chamber 12 that allows fluid communication therebetween. As shown in FIG. 1, fill channel 16 is a conduit or passageway positioned between the reservoir 14 and sample chamber 12. The fill channel can have any suitable cross-sectional shape, such as, for example, circular, square, or rectangular. The fill channel is preferably sized to allow the biological sample to flow from the reservoir 14 into the sample chamber 12 when such flow is desired. As will be discussed further, fill channel may be selectively blocked in order to prevent fluid communication between the reservoir 14 and sample chamber 12.

In various embodiments, first and second members 10a and 10b further include concave portions 12a and 12b, respectively. In a first position (shown in FIGS. 2a and 2b), concave portion 12b of the second member mates with and is in direct contact with concave portion 12a of the first member. In this first position, the first and second concave portions are in direct contact, therefore there is no space between the portions for liquid sample. The concave portion 12b of the second member is configured to be movable with respect to concave portion 12a of the first member to define a volume of space therebetween that will comprise sample chamber 12, when the concave portion of the second member is in a second position. In this second position, the concave portion 12a of the first member defines the sample chamber base. This will be described in more detail below.

Figure 2A:
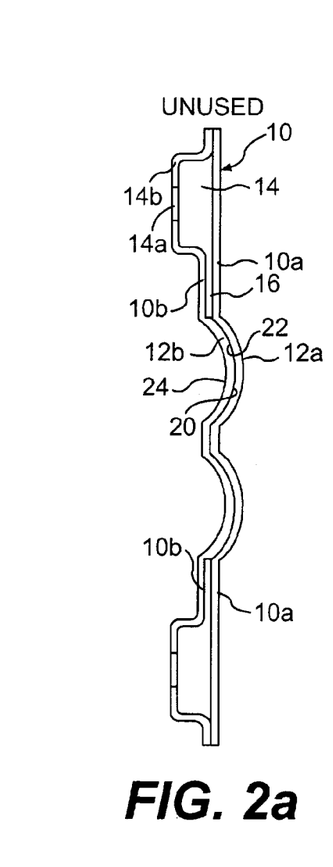
FIGS. 2a-2e are a series of cross-sectional views along section line II-II of the sample chamber array of FIG. 1 showing a sequential operation of loading, filling, sealing, and trimming the sample chamber array.

FIG. 2a shows an unloaded sample chamber array 10 according to an embodiment of the present teachings. In FIG. 2a, no liquid sample has been introduced into the reservoir 14. In FIG. 2a, the concave portion 12b of the second member is in a first position wherein the inner surface 20 of the concave portion 12b presses against and mates with an inner surface 22 of the concave portion 12a of the first member.

Figure 2B:
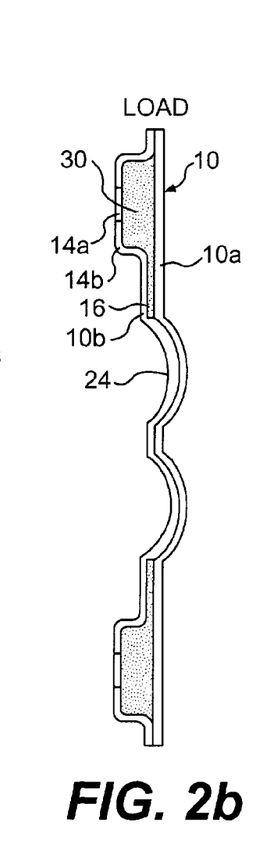

FIG. 2b shows the sample chamber array with a liquid sample 30 to be tested contained in the reservoir 14 and fill channel 16. The liquid sample 30 may be introduced into the reservoir by any known method. In one embodiment, a user may introduce a sample 30 into reservoir 14 via fill port 14a by for example, pipetting the sample through the fill port 14a. In another embodiment, the sample 30 may be introduced into reservoir 14 via active or passive transport known in the art of microfluidics. Sample 30 may comprise both a sample and a reagent that is already pre-mixed or sample chamber 12 may be spotted with a dried reagent for reaction with sample 30 once sample 30 flows into chamber 12. As shown in FIG. 2b, the sample 30 fills the reservoir 14 and fill channel 16. The sample 30, however, is obstructed from flowing between the concave portions 12a and 12b because the inner surfaces of the concave portions are pressed firmly against each other. The concave portions are pressed firmly against each other because of the particular shape of the concave portions. In the position shown in FIGS. 2a and 2b, the concave portions are preferably biased to engage each other with sufficient force to prevent the passage of liquid between the concave portions.

Figure 2C:
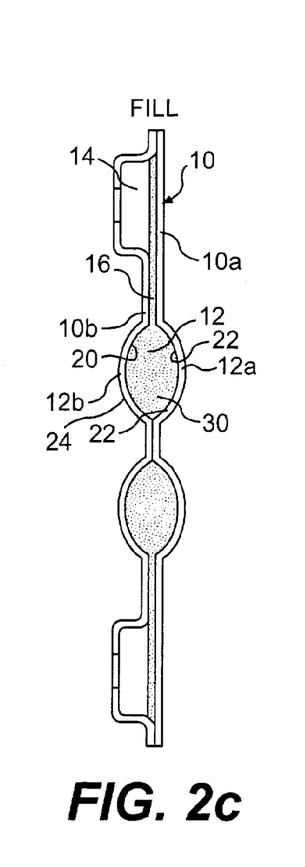

When it is desired to form sample chambers for the liquid sample, the user may move concave portion 12b of the second member away from the concave portion 12a of the first member, thereby creating sample chamber 12 as shown in FIG. 2c. In certain embodiments, such as shown in FIG. 2c, the concave portion 12b of the second member may be moved away from concave portion 12a of the first member by inverting the concavity of concave portion 12b, thereby forming sample chamber 12. In the second position, shown in FIG. 2c, portion 12b is convex in shape.

The inversion of portion 12b creates an internal suction, or pressure drop, between the newly formed sample chamber 12 and reservoir 14, thereby causing the liquid sample 30 to flow from reservoir 14 into sample chamber 12 via fill channel 16. The movement of concave portion 12b of the second member away from concave portion 12a of the first member may be accomplished by any of a variety of methods. In one embodiment, the sample chamber array is placed on a vacuum chuck, or other suitable device, capable of applying external suction or other force to the outside surface 24 of concave portion 12b of sample chamber array 10 sufficient to cause the concave portion 12b of the second member to snap or move away from the concave portion 12a of the first member, into the position depicted in FIG. 2c. In one embodiment, the vacuum chuck may be a substantially flat plate with a plurality of holes corresponding to the sample chambers of the sample chamber array. The holes may be configured so that they align with the sample chambers of the sample chamber array. The holes may be any suitable size. In one embodiment, the holes have a diameter approximately the same as the diameter of the sample chambers. The vacuum chuck can be any suitable material, for example, metal. The vacuum chuck may be configured to draw a vacuum in the holes upon contacting the sample chamber array, in order to create an adequate suction force to cause the concave portion 12b of the first member to snap or move away from the concave portion 12a of the second member. Appropriate sealing structure may also be provided.

In the embodiment shown, the concave portion 12b automatically snaps from a first discrete position (shown in FIG. 2b) to a second discrete position (shown in FIG. 2c) when a sufficient force is placed on the outer surface 24 of the concave portion 12b. In another embodiment, portion 12b is made of material that is sensitive to heat and/or electrical current, where application of such to portion 12b causes inversion. For example, portion 12b can be made of nitinol, other alloys, or polymers known in the art of shape-memory materials.

When the concave portion 12b of the second member snaps into the position shown in FIG. 2c, the sample chamber 12 is formed in the space between the concave portion 12a and the concave portion 12b. In the position shown in FIG. 2c, the concave portion 12a of the first member 10a may be referred to as the sample chamber base. The sample chamber 12 shown in FIG. 2c has a bulbous shape. It should be understood that any other suitable shape is also acceptable for the sample chamber. The sample chamber may be designed to handle any suitable volume of biological sample.

Although depicted as having the movable portion 12b on the same side of the card as fill opening 14a (e.g., on the second member), the concavity of portions 12a and 12b may face in the opposite direction as that depicted in FIG. 2a so that the vacuum, or other force, applied to portion 12b can be applied on portion 12a instead.

Figures 2D, 2E:
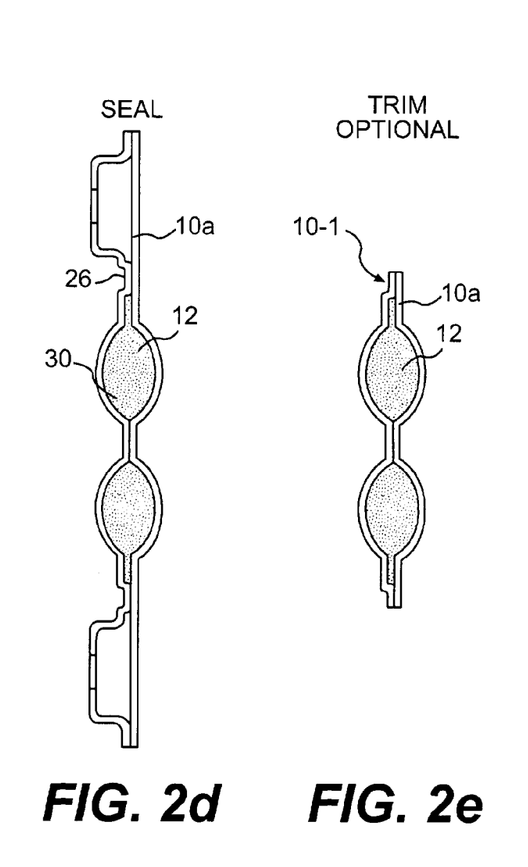

Once sample chambers 12 are filled with the desired sample 30, fill channel 16 may be staked or otherwise sealed along region 26, as shown in FIG. 2d, so that sample 30 does not leak out of sample chamber 12. As mentioned above, this sealing may be accomplished by applying pressure to one side of sample chamber array 10 along channel 16 so that a portion of one of the first or second members 10a, 10b in the area of region 26 adheres to adhesive member 18 located between members 10a, 10b as depicted in FIG. 1. FIG. 2d shows the fill channel 16 closed after a staking operation. Staking may also be accomplished by using a foil backing, or other suitable material, in one of members 10a and 10b at least in the area of channel 16 so that a stylus or other suitable device can deform a portion of the foil and create a seal along channel 16. In the position shown in FIG. 2d, sample chamber 12 is sealed, therefore no sample can leave or enter the sample chamber.

Figure 3:
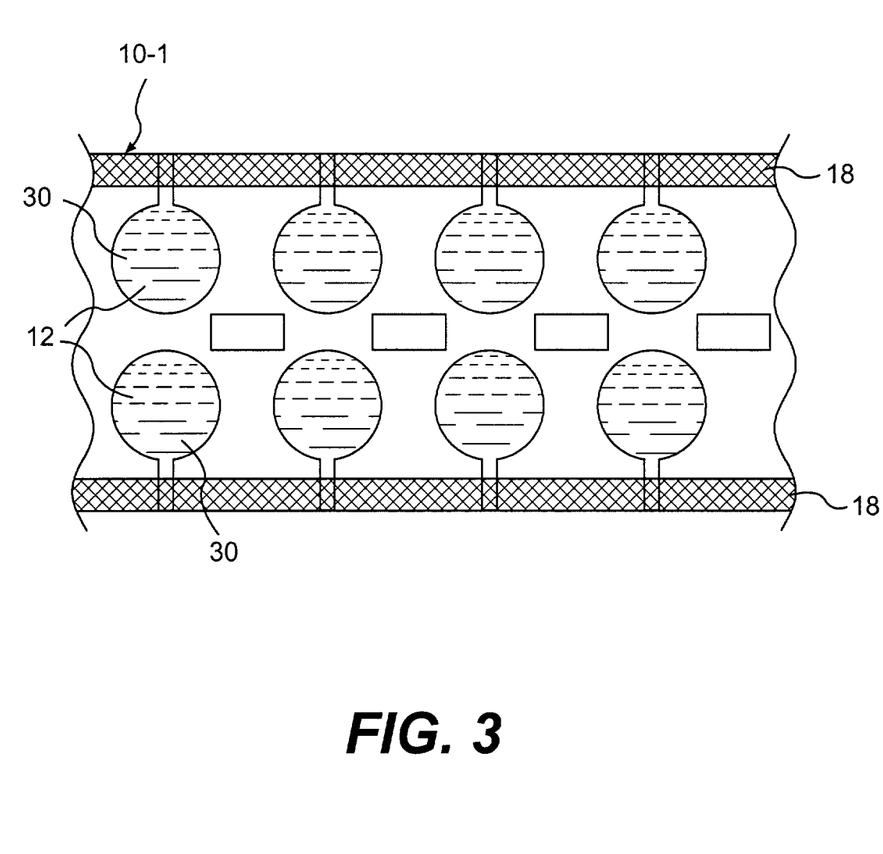
FIG. 3 is a partial plan view of the sample chamber array of FIG. 2e.

Although it is not necessary to dispose of the portion of array 10 containing reservoirs 14, as shown in FIG. 2e, it may be desirable to trim these sections from array 10, for example, so that the size of the actual array 10-1 that is to be tested is smaller than the array 10 containing the reservoirs 14. FIGS. 2e and 3 show a sample chamber array 10-1 in which the portions of the array containing reservoirs have been trimmed from the sample chamber array. The portions of the array containing reservoirs may be trimmed by any suitable cutting method. The trimmed sample chamber array 10-1 is ready to be tested in a suitable PCR testing device.

As is clear from the above description, the present teachings include methods for processing a biological sample. The method comprises providing a sample chamber array comprising at least one reservoir in fluid communication with at least one sample chamber, filling the reservoir with the biological sample, and moving the sample chamber from a concave position to a convex position. The moving of the sample chamber generates a pressure drop to transport the biological sample from the reservoir to the sample chamber.

The present teachings further include methods of making a sample chamber array. The method comprises providing a first member comprising at least one chamber base, providing a second member comprising at least one movable portion, positioning the first member and the second member to align the chamber base and the movable portion, and affixing the first member to the second member. The affixing the first member to the second member forms at least one reservoir between the first member and the second member. In various aspects, the chamber base and the movable portion are concave.

Figure 5:
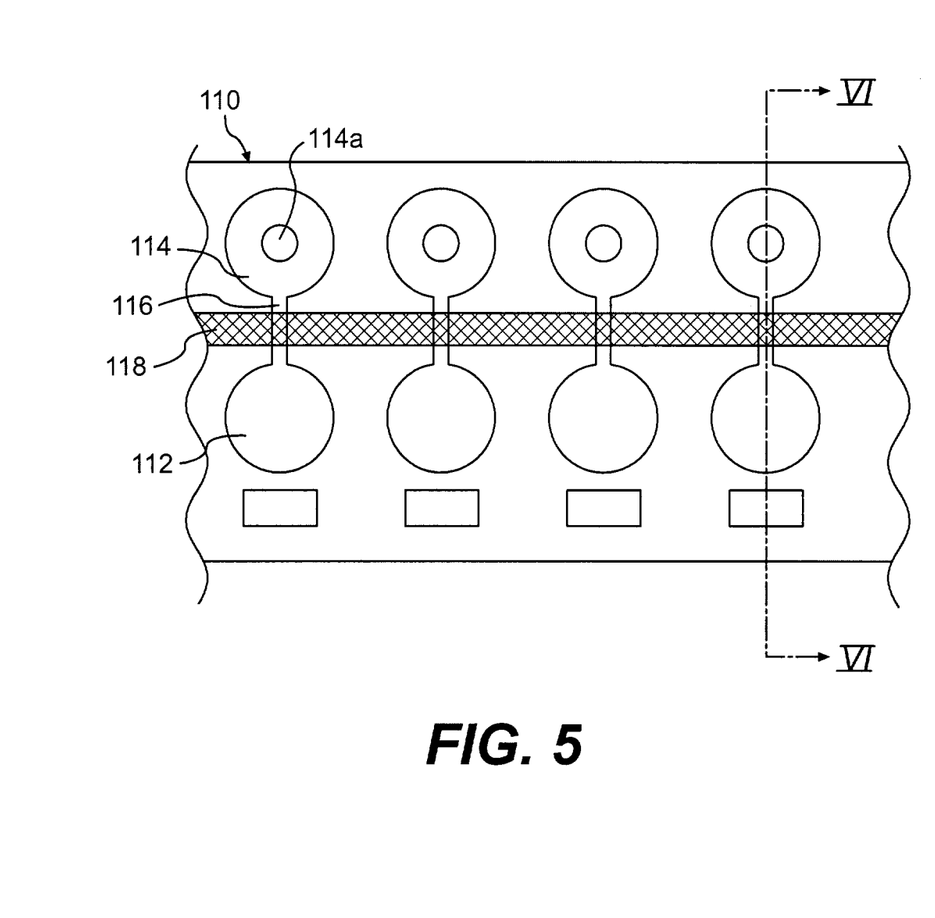
FIG. 5 is a partial plan view of a section of a sample chamber array according to another exemplary embodiment.
Figure 6A:
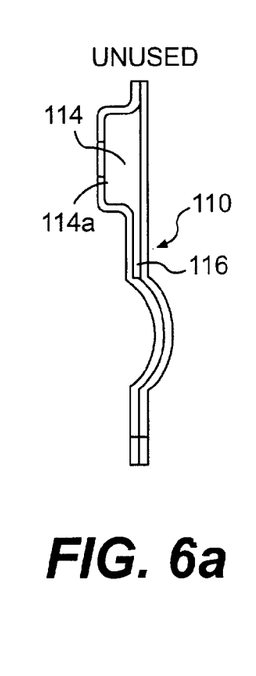
FIGS. 6a-6e are a series of cross-sectional views of the sample chamber array along section line VI-VI of FIG. 5 showing a sequential operation of loading, filling, sealing, and trimming the sample chamber array.
Figure 6B:
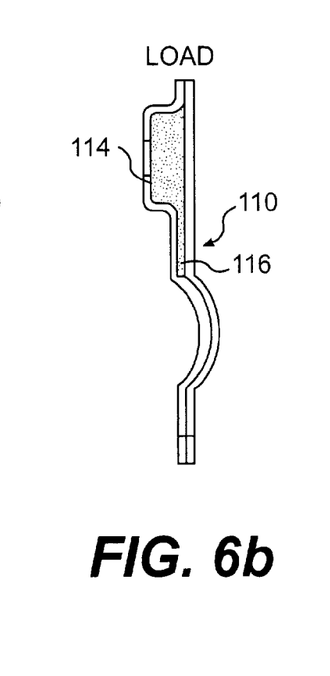
Figure 6C:
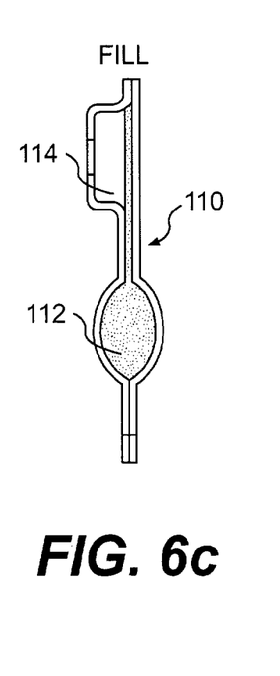
Figure 6D:
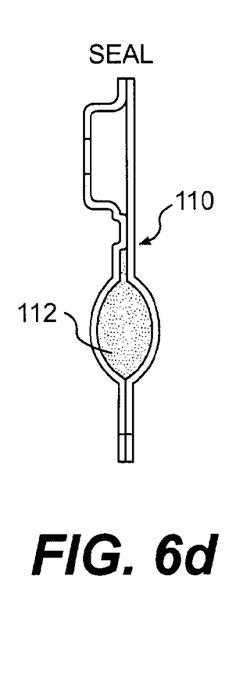
Figure 6E:
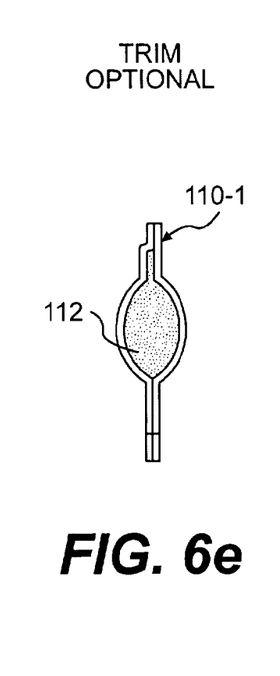
Figure 7:
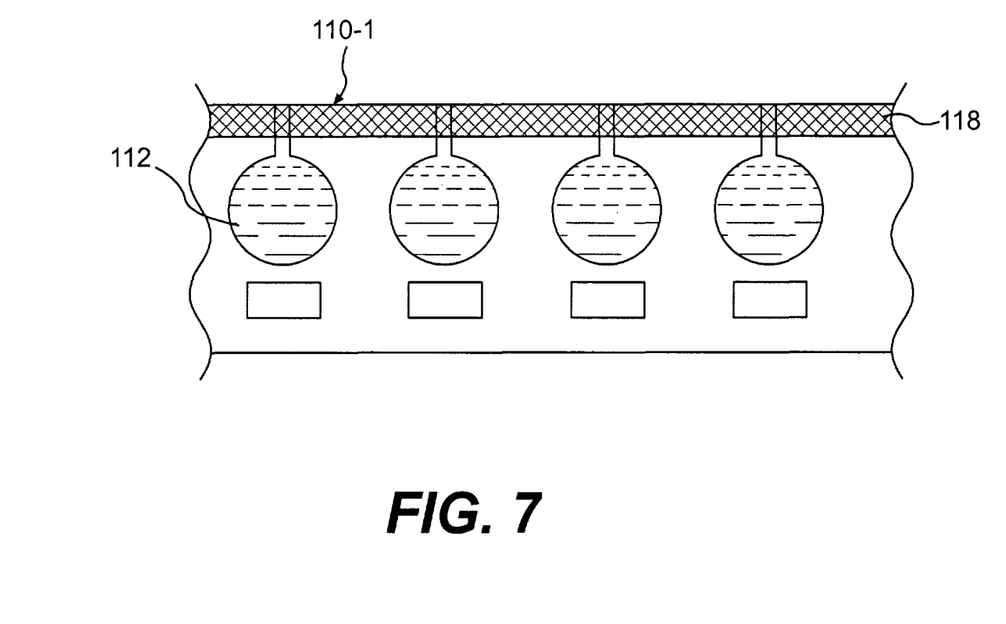
FIG. 7 is a partial plan view of the sample chamber array of FIG. 6e.

According to another exemplary embodiment of the present teachings, a sample chamber array may be provided with any number of rows. FIG. 5 shows a sample chamber array 110 comprising only a single row of sample chambers 112, reservoirs 114, and fill channels 116. The reservoirs 114 are identical to those shown in FIGS. 1-4, including fill ports 114a. Sample chamber array 110 also includes an adhesive strip 118 to aid in the staking or sealing of chambers 112 once they have been filled. The sample chambers 112 and fill channels 116 are also identical to those shown in FIGS. 1-4. FIGS. 6a-6e illustrate the filling and trimming operation of sample array 110. The steps are identical to those discussed above with respect to FIGS. 2a-2e, and will not be repeated. FIG. 7 depicts a trimmed and filled sample array 110-1 of FIG. 6e.

Figure 8:
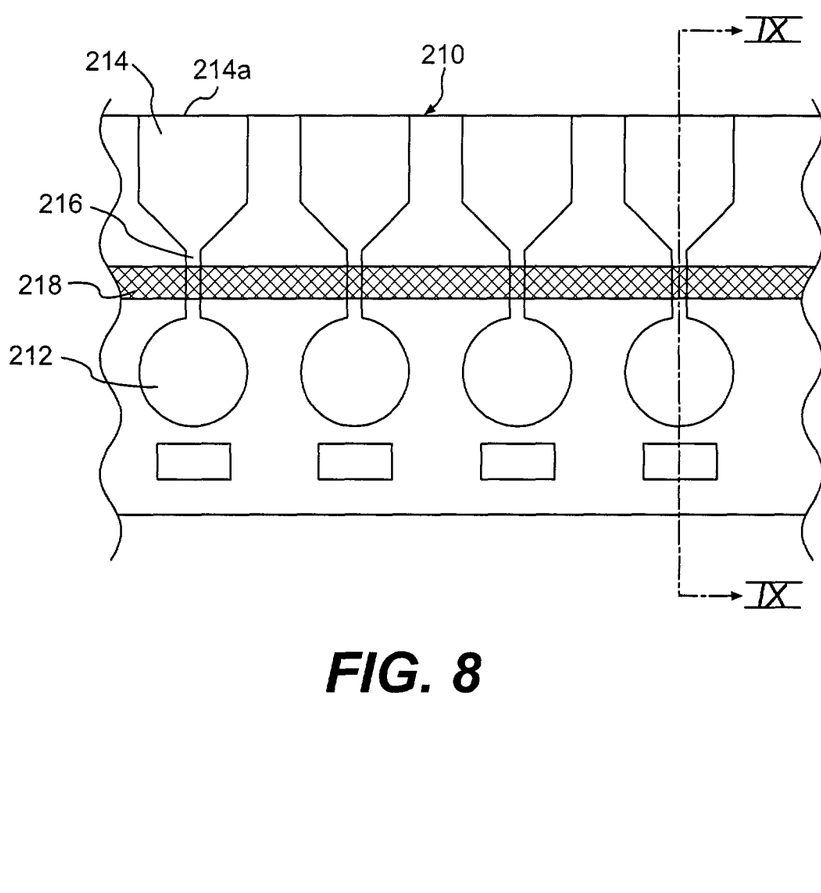
FIG. 8 is a partial plan view of a section of a PCR sample chamber array according to another exemplary embodiment.

According to another exemplary embodiment of the present teachings, a sample chamber array may be provided with a plurality of reservoirs suitable for vertical orientation. As shown in FIG. 8, sample array 210 may include a plurality of sample chambers 212 and reservoirs 214 in fluid communication via fill channels 216. Sample chamber array 210 also includes an adhesive strip 218 to aid in the staking or sealing of chambers 212 once they have been filled. Reservoirs 214 include openings 214a configured to facilitate filling of reservoirs 214 with sample array 210 in a substantially vertical position. The reservoirs 214 have a generally funnel-like shape, although any other suitable shape may be used. Although array 210 utilizes a different reservoir configuration, the filling of chamber 212 as depicted in FIGS. 9a-9e is accomplished in a similar fashion as that of arrays 10 and 110.

Figure 9A:
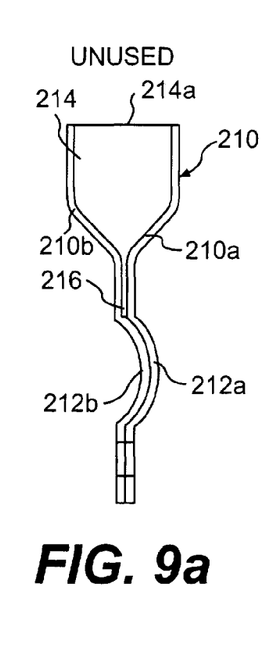
FIGS. 9a-9e are a series of cross-sectional views of the sample chamber array along section line IX-IX of FIG. 8 showing a sequential operation of loading, filling, sealing, and trimming the sample chamber array.
Figure 9B:
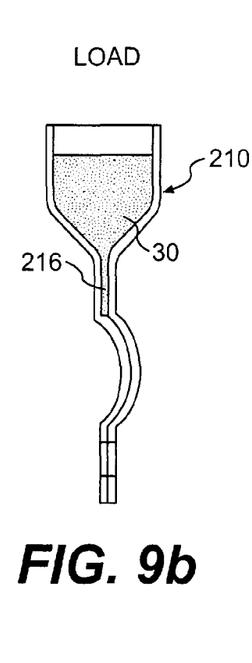
Figure 9C:
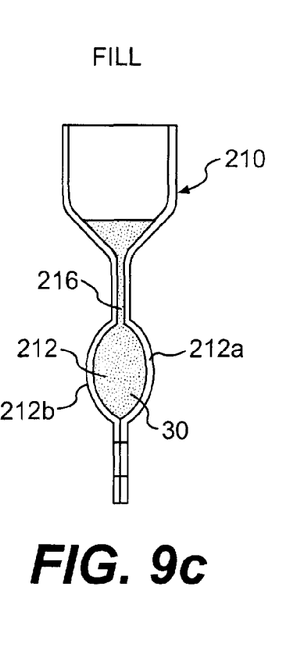
Figure 9D:
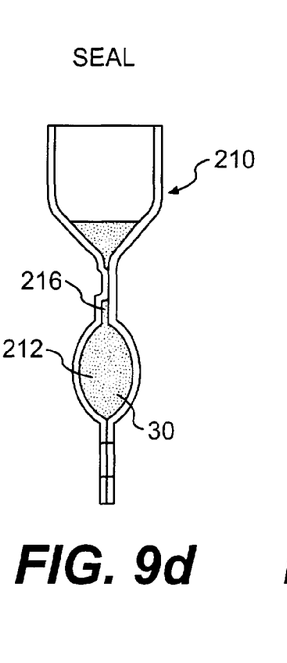
Figure 9E:
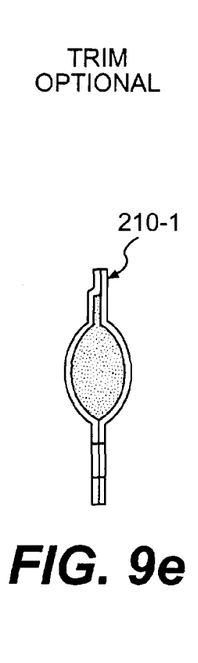
Figure 10:
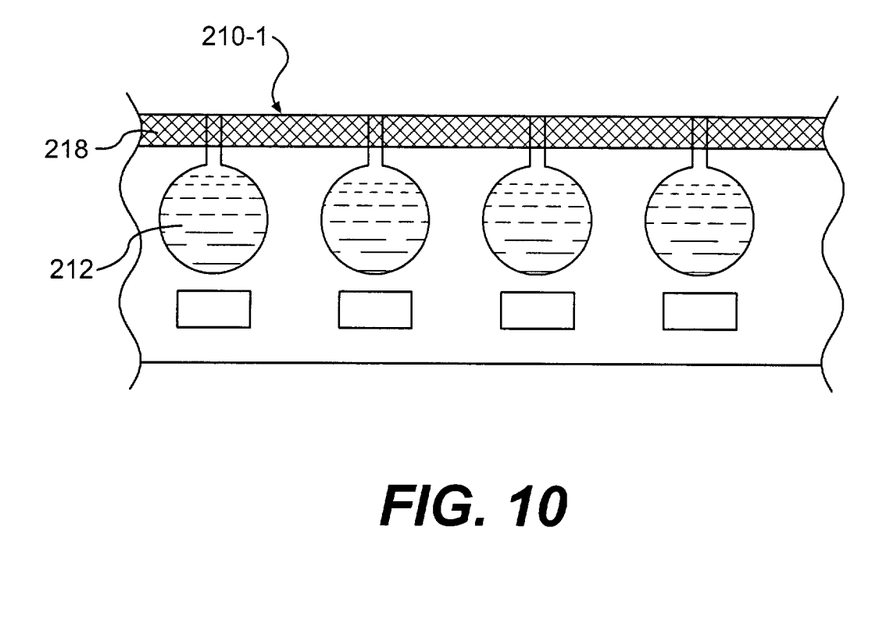
FIG. 10 is a partial plan view of the sample chamber array of FIG. 9e.

FIGS. 9a-9e shows the operation of loading, filling, sealing, and trimming the sample chamber array of FIG. 8. FIG. 9a shows the sample array 210 with no fluid sample introduced into reservoir 214. FIG. 9b shows the reservoir 214 filled with fluid sample. FIG. 9c shows the sample array after the concave portion 212b of second member 210b has had its concavity inverted so that it is spaced from concave portion 212a of the first member. The liquid sample fills the sample chamber 230 as shown in FIG. 9c. FIG. 9d shows the sample array 210 after sealing of the fill channel 216 via the method discussed for FIG. 2d. FIGS. 9e and 10 shows the trimmed sample array 210-1. Trimmed array 210-1 shown in FIGS. 9e and 10 may be identical to array 110-1 shown in FIGS. 6e and 7.

Figure 11:
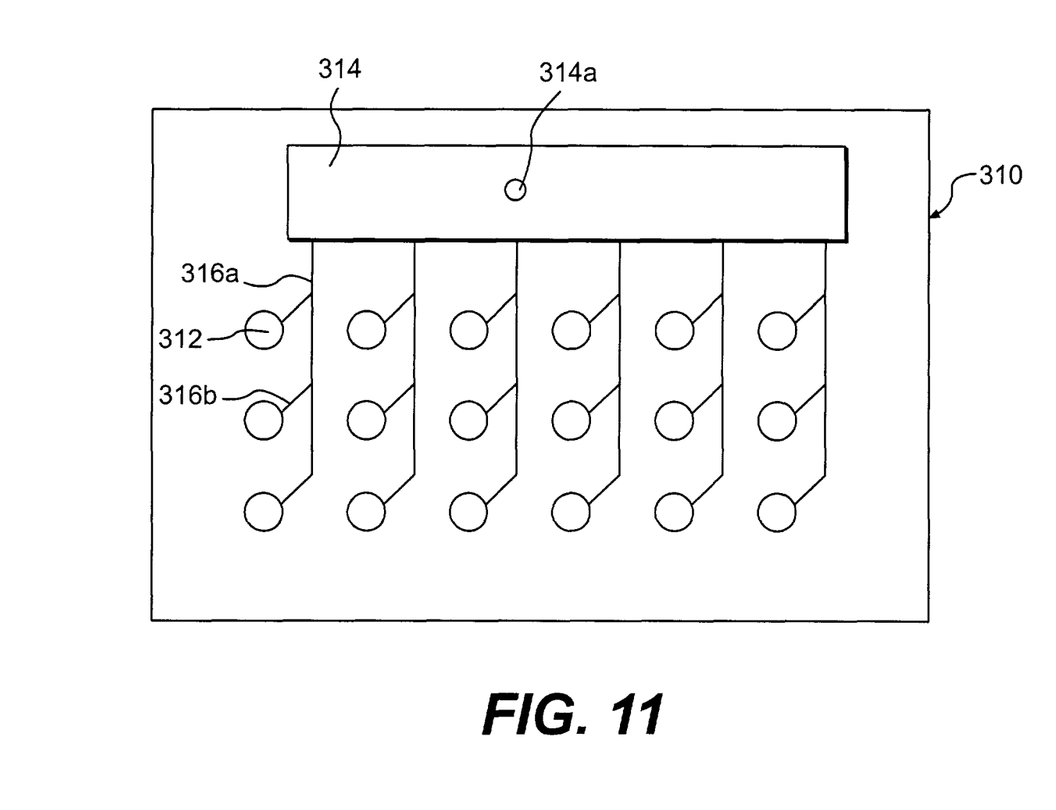
FIG. 11 is a plan view of an exemplary embodiment of a sample chamber array having a single reservoir feeding multiple chambers.

According to another exemplary embodiment of the present teachings, a sample chamber array may include a plurality of main channels and branch channels. As shown in FIG. 11, a sample array 310 has a single reservoir 314 for a plurality of sample chambers 312. The reservoir 314 includes a single fill opening or fill port 314a, although multiple fill openings may be provided. Although sample reservoir 314 is depicted having fill port 314a positioned for horizontal filling of sample array 310, reservoir 314 could also have a reservoir similar to reservoir 214 of FIGS. 8-10 that would be open along at least a portion of the upper edge of reservoir 314 and would allow for vertical filling of sample array 310. Sample array 310 includes six main fill channels 316a, each associated with a plurality of sample chambers 312. Main fill channels 316a communicate with sample chambers 312 via branch channels 316b.

As with previous embodiments, each of sample chambers 312 may include a movable portion that creates suction within sample chamber 312, thus drawing fluid into the sample chambers via channels 316a, 316b. After filling, sample chambers 312 may then be sealed off from reservoir 314, for example, by use of an adhesive strip similar to adhesive strip 18, or sample array 310 may include a deformable material that would allow staking as described above, among other sealing means or methods. In one embodiment, reservoir 314 feeds multiple sample chambers and has a volume at least as great as the number of sample chambers 312 it serves. In another embodiment, the fluid drawn toward each of sample chambers 312 remains in the channels 316a and 316b, and concave portions of sample chambers 312 expand to a volume larger than the actual volume desired for testing.

For example, if a user desired to fill each of sample chambers 312 with 5 µL and the total volume of one of channels 316a and its corresponding branch channels 316b comprised 3 µL, then it may be desirable for each of chamber 312 be capable of expanding to 6 µL or more. With this configuration, when the concave portions of chambers 312 are inverted, as described with reference to FIG. 2c for example, the three chambers will create suction capable of drawing a total of 18 µL from reservoir 314. Accordingly, 5 µL may flow into each of chambers 312 leaving 3 µL in main channel 316a and branch channels 316b. Although sample array 310 is depicted having a single reservoir 314 associated with all of sample chambers 312, array 310 may include multiple reservoirs each associated with a predetermined number of sample chambers 312. In addition, although branch channels are depicted, array 310 may comprise one or more main feed channels without branch channels. In this configuration, fluid would flow through each subsequent sample chamber to reach the last chamber and so on until each chamber is filled.

In one method of filling the sample chambers of FIG. 11, it may be desirable to invert the concave portions of the sample chamber 312 in a predetermined pattern. For example, in one embodiment, it may be desirable to invert the sample chambers farthest from the reservoir first, and then sequentially invert the sample chambers closer to the reservoir in a sequential manner. This may help to minimize the occurrence of air bubbles in the sample chambers caused by the process of filling. In another method of filling the sample chambers of FIG. 11, it may be desirable to prefill the main fill channels 316a prior to inverting the concave portions of the sample chambers 312. The main fill channels may be filled with the biological sample in any known manner, such as vacuum loading, centrifugal loading, and capillary action. After the main fill channels are filled with biological sample, any remaining air bubbles may be vented through an appropriate vent on the main fill channels. The concave portions of the sample chambers may then be inverted, causing the biological sample to flow from the main fill channels into the sample chambers. This method may also assist in minimizing the potential for air bubbles in the sample chambers.

Figure 12:
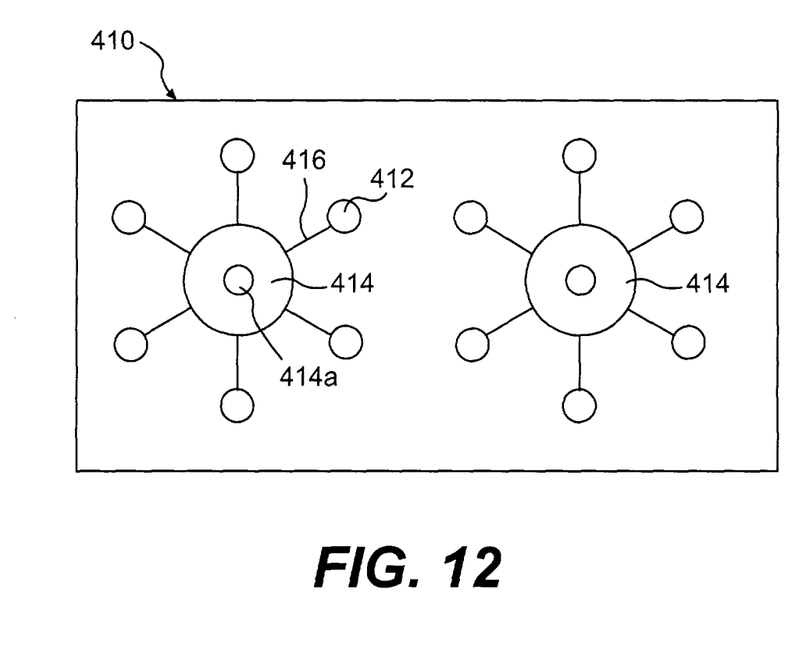
FIG. 12 is a plan view of an exemplary embodiment of a sample chamber array having a pair of reservoirs each feeding a plurality of radially positioned sample chambers.

According to still another exemplary embodiment of the present teachings, a sample chamber array may be provided with a plurality of sample chambers for each reservoir. As shown in FIG. 12, a sample chamber array 410 includes a pair of reservoirs 414. Each reservoir has a fill opening or fill port 414a to allow for filling of the reservoir. Each reservoir 414 feeds a plurality of sample chambers 412, in this case six, via an equal number of fill channels 416. It should be noted, however, that more or fewer chambers may be associated with each reservoir and also that a single feed channel 416 may be associated with more than one chamber 412 as it extends away from reservoir 414. In the embodiment shown in FIG. 12, the sample chambers 412 are positioned radially surrounding from reservoir 414. It should be understood that the sample chambers may be positioned in any configuration relative to the reservoir.

The embodiments described herein are not intended to describe all possible configurations in number and size of sample chambers, channels, and reservoirs. Sample arrays of various sizes and shapes could be used that include the snap-action detail for filling as disclosed herein. It will be apparent to those skilled in the art that various modifications and variations can be made to the structure and methods described above. Thus, it should be understood that the present teachings are not limited to the examples discussed in the specification. Rather, the present teachings are intended to cover modifications and variations.

What is claimed is:

1. A sample chamber array, comprising:
a first member affixed to a second member, wherein the first member and second member comprise a flexible material;
a first concave-shaped portion of the first member mated with an invertible second concave-shaped portion of the second member, wherein the first and second concave-shaped portions are configured to be biased to engage each other with sufficient force to prevent the passage of fluid between the concave-shaped portions, and wherein the first and second concave-shaped portions are further configured to form a sample chamber when the second concave-shaped portion is moved from a concave shape to a convex shape; and
at least one reservoir in fluid communication with the sample chamber when the second concave-shaped portion is moved to the convex shape, wherein said at least one reservoir is fillable with a liquid biological sample, wherein the formation of the sample chamber between the first and second concave-shaped portions causes a pressure drop between the at least one reservoir and the formed sample chamber thereby transporting said biological sample into said formed sample chamber from said at least one reservoir and
a device configured to apply an external suction, at a predetermined force, to an outside surface of the invertible second concave-shaped portion of the second member to invert the invertible second concave-shaped portion of the second member.

2. The sample chamber array of claim 1, further comprising a fill channel for said fluid communication between said reservoir and said sample chamber.

3. The sample chamber array of claim 2, further comprising an adhesive element to allow for closure of the fill channel, wherein the adhesive element is located in the fill channel between the first and second members.

4. The sample chamber array of claim 2, wherein the first and second members define the fill channel and comprise a deformable material configured to be deformed to close fluid communication between said reservoir and said sample chamber.

5. The sample chamber array of claim 1, further comprising a plurality of sample chambers that extend radially from the at least one reservoir.

6. The sample chamber array of claim 2, further comprising a plurality of sample chambers and a plurality of branch channels in fluid communication between the fill channel and the plurality of the sample chambers.

7. The sample chamber array of claim 1, wherein the at least one reservoir further comprises a fill opening for filling the reservoir with said biological sample.

8. The sample chamber array of claim 7, wherein the fill opening for the at least one reservoir is on a first side of the at least one reservoir opposite the sample chamber to facilitate filling of the at least one reservoir with the sample chamber array in a substantially vertical position such that, in the substantially vertical position, the fill opening is on top of the reservoir and the sample chamber is below the fill opening.

9. The sample chamber array of claim 1, wherein the sample chamber array is provided as a rollable tape.

10. The sample chamber array of claim 1, wherein said sample chamber array comprises at least one of polypropylene and polyethylene.

* * * * *